United States Patent [19]
Pfeffer

[11] Patent Number: 6,159,131
[45] Date of Patent: Dec. 12, 2000

[54] FITNESSTRIAGE SYSTEM AND METHOD

[75] Inventor: Linda Pfeffer, Los Angeles, Calif.

[73] Assignee: Aerobics and Fitness Association of America, Sherman Oaks, Calif.

[21] Appl. No.: 09/360,617

[22] Filed: Jul. 26, 1999

[51] Int. Cl.$^7$ .................................................. A63B 71/00
[52] U.S. Cl. ................... 482/8; 434/236; 128/920
[58] Field of Search .................. 482/8; 434/236–238; 128/920, 923

[56] References Cited

U.S. PATENT DOCUMENTS

| | | | |
|---|---|---|---|
| 5,722,418 | 3/1998 | Bro | 482/9 |
| 5,961,332 | 10/1999 | Joao | 434/236 |

*Primary Examiner*—Glenn E. Richman
*Attorney, Agent, or Firm*—Patrick F. Bright

[57] ABSTRACT

Fitness Triage® is a system and method for prioritizing delivery of personalized exercise and injury prevention information based on identification and analysis of user-specific health and fitness indicators. By providing answers to questions concerning key health risk factors, conditions, and habits, exercise information is delivered to the user based on the level of potential risk and other considerations associated with his/her participation in an exercise program. Based on the Fitness Triage® analysis of user data, the delivery of information is identified and prioritized according to one of three levels of potential risk. The user is thus informed of the level of risk associated with his/her participation in exercise, and the recommended precautions based on his/her individual health profile. The Fitness Triage® system is accessed by the user directly through the Internet or licensed Intranet, or through the guidance of an intake coordinator, personal trainer, or other qualified health/fitness professional.

9 Claims, 3 Drawing Sheets

FITNESS TRIAGE

FITNESS TRIAGE

FITNESS TRIAGE ®

FITNESS GETS PERSONAL® INFORMATION SEARCH WITH RETURN TO FITNESS TRIAGE®

FITNESS TRIAGE SYSTEM AND METHOD

BACKGROUND OF THE INVENTION

The invention relates to the field of exercise science and individualized identification and enhancement of potential exercise benefits and prevention of exercise related injury according to individual habits and health risk indicators.

On Jul. 11, 1996, the U.S. Surgeon General's Report on Physical Activity and Health was released to the public. The publication of this report culminated over 20 years of research supporting the health risks associated with inactivity and conversely, the health benefits associated with regular exercise. Today, largely as a result of this report, every health maintenance organization and major indemnity insurer in the U.S. encourages its insured to increase physical activity as a means of promoting overall wellness and preventing disease. Additionally, since release of the Surgeon General's Report, the media has consistently delivered the message to both health providers and consumers, that exercise should be included as a part of each individual's wellness routine. However, reliable information on how to implement an individualized program of physical activity is not always available through insurance companies, health maintenance organizations, or private health care providers.

To fulfill the need for guidance in physical activities, many Americans are joining health clubs in ever-increasing numbers. U.S. health club membership in 1987 was 13.7 million. By the close of 1999, that number is projected to reach 25 million. However, the adjusted attrition rate, after accounting for health club members who move, is approximately 25%. Thus, despite increased health club memberships, only 30% of the U.S. adult population exercise regularly in any setting.

According to research, the availability of compelling data relating to the benefits of exercise is a key factor in exercise compliance. Starting and maintaining a fitness program involves behavioral changes structured to individual needs. For instance, an individual with chronic knee pain requires information and/or instruction specific to his/her condition in order to ensure that his/her exercise program is both safe and effective. Similar information is important for a wide variety of conditions such as high blood pressure, arthritis, obesity, and pregnancy. Additionally, reliable data regarding correct exercise methods is equally important to healthy individuals in both starting and maintaining an exercise program.

Prior to the introduction of the Fitness Triage® system, there was no program that provided individualized identification, evaluation and prioritized delivery of exercise information and precautions according to an established database of researched information.

SUMMARY OF THE INVENTION

The Fitness Triage® invention fills this void by providing consumers and professionals a reliable system, program and method of access that provides individualized identification, evaluation and prioritized delivery of exercise information and precautions according to an established database of researched information.

The invention enables the user/consumer to access reliable information regarding his/her actual/planned exercise experience, thus enhancing the potential for both safe and effective physical activity, and exercise adherence.

The invention enables the user to access this information directly or through a qualified health/fitness professional who directs the data entry. Methods of access include direct access through the Internet for a small fee associated with membership or subscription; access through an intake coordinator via phone for a small fee; and access directed by a qualified professional at a non-determined fee.

The invention also provides the user with the opportunity to reevaluate user's initial results based on health or behavioral changes.

BRIEF DESCRIPTION OF THE DRAWINGS

FIG. 1

1.A User accesses the Fitness Triage® system through the Internet at the website of the Aerobics & Fitness Association of America, www.afaa.com. All users are provided with a login number (username). Each user then creates his/her own password. The individual who accesses the Fitness Triage® system may do so for his/her own information, or acting on behalf of another. A personal trainer or physician are examples of professionals who may utilize the service on behalf of another.

As a user initiates the login process, the program will first recognize whether or not the user has a valid login number (username). If the login number is valid, and this is a first login for the user, the program will request that the user create a personal password. Return users with a valid login number will enter both their username and password to complete the login process. Invalid login numbers are rejected.

Figure 1:
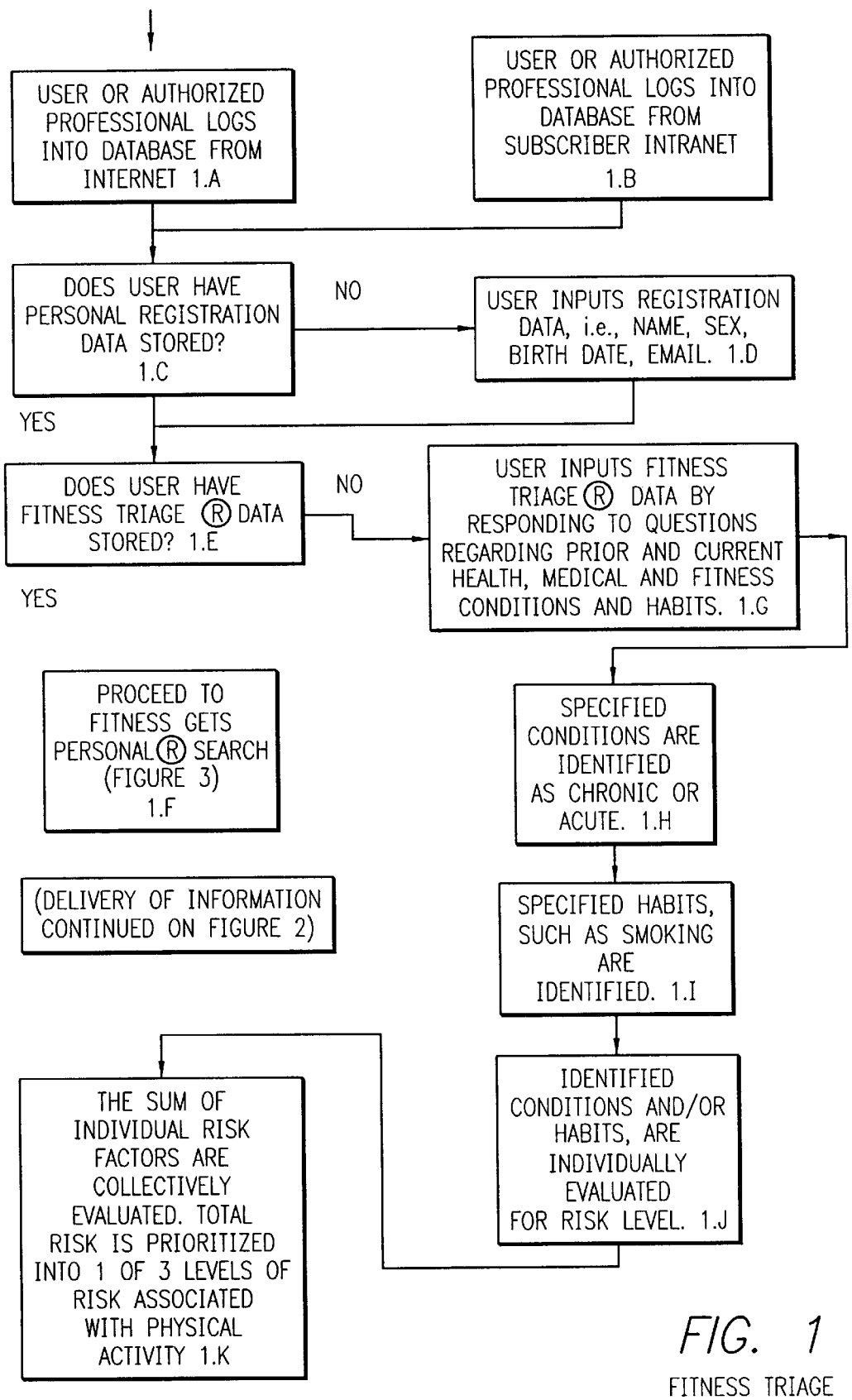
FIG. 1 describes the data input and analysis stages of the Fitness Triage® system process.
Figure 2:
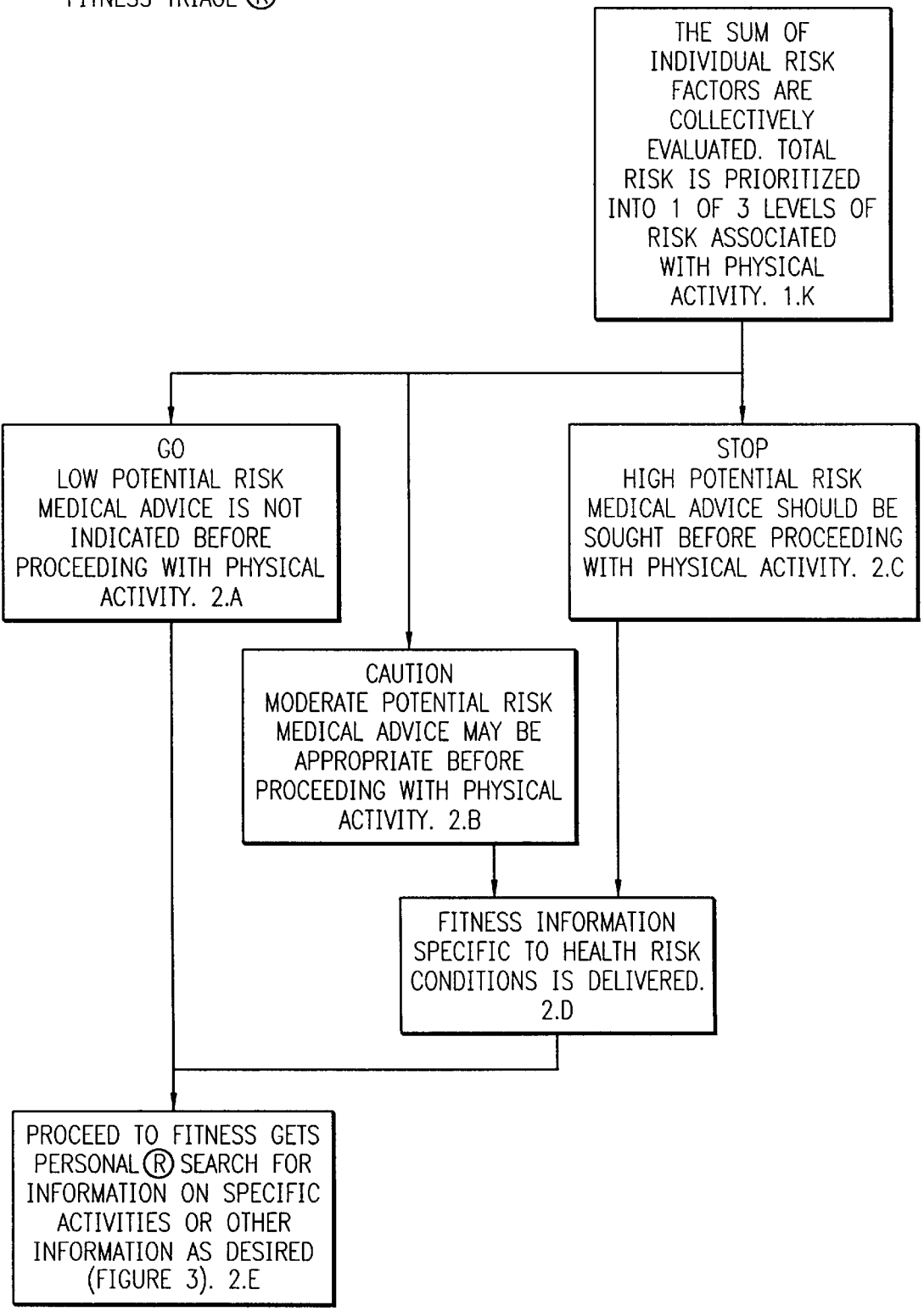
FIG. 2 describes prioritization of potential risk and the delivery of information.

1.B User accesses the Fitness triage® system through a corporate Intranet. AFAA sells corporate subscription packages which allow corporations to provide employees or health/fitness professionals with access to the Fitness Triage® system through either the Internet or through the corporate Intranet. All other aspects of access are the same as described for FIG. 1.A.

1.C Upon completing login, the program will recognize whether or not the user has personal registration data stored. Personal registration data for each user is stored in a database on the AFAA server.

1.D If the program does not find any stored registration information, the user will be requested to complete a brief registration form. Completion of all fields is required. The fields include; first and last name, birth date, gender, and email address.

1.E After valid registration is acknowledged, the program will recognize whether or not the user has Fitness Triage® data stored. Personal health data obtained through the Fitness Triage® system is stored for each user in a database on the AFAA server.

Figure 3:
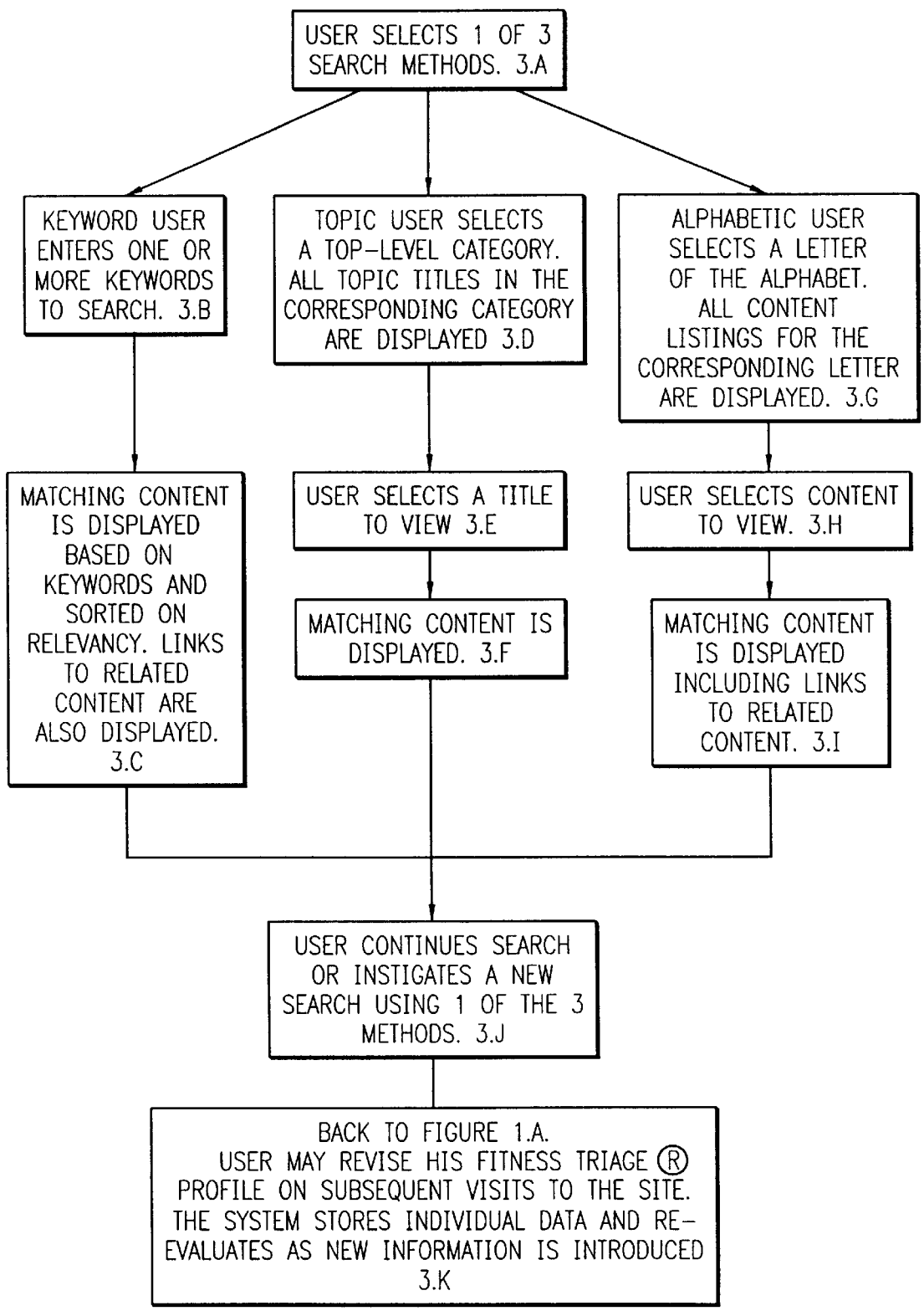
FIG. 3 describes the final process of the user's search for and delivery of discretionary information.

1.F If the user has previously completed the Fitness Triage® he/she may proceed directly to the Fitness Gets Personal® search (see FIG. 3).

1.G If the program does not find any stored health information, the user will be requested to complete a brief health questionnaire. The questionnaire is divided into 7 sections. In the first 4 sections the user simply selects items that apply from the lists provided. The first section requests information about current condition or habits that relate to overall risk. The second section gathers information related to medical care or clearance. The third section gathers information about any current health concerns. The fourth section gathers health history and chronic disease/condition information. In section five the user is asked to list current medications. In section six the user lists other medical conditions, if any, that were not included in the list provided. Finally, the user is asked the date of his/her last medical exam. The user then submits the form. This is a secure transmission using SSL technology.

1.H The program scans the medical conditions such as illness or injury submitted and identifies those items which are chronic, acute, and/or symptomatic.

1.I The program scans the habits and other health-related conditions submitted and identifies the any that may pose a risk, i.e., smoking or pregnancy.

1.J All conditions and habits are individually evaluated for level of potential risk. Each is assigned a numerical weighted value. For example, an affirmative response to the query "Recent Surgery/Wound" is weighted more heavily than an affirmative response to "Tobacco Use".

1.K The sum of all individual weighted values is evaluated collectively, analyzing the total risk of all conditions in conjunction with one another. In other words, the individual effect of one condition may create a moderate risk potential. However, that condition accompanied by one or more other conditions, may create a high risk potential. Likewise, an affirmative response to the query, "Are you cleared by a physician to exercise?" may reduce the level of overall risk. This portion of the Fitness Triage® process analyzes all possible combinations and prioritizes the information that will be delivered to the user according to 1 of 3 levels of potential risk associated with physical activity. The user is delivered a message that indicates the level of risk according to his personal indicators.

[LP: CAN WE STATE OUR GENERIC WEIGHING FORMULAE)?]

FIG. 2

2.A. The first level of risk that is identified in the Fitness Triage® system is that of low potential risk. Medical advice is not indicated before proceeding with physical activity. This is graphically indicated to the user by use of a green "GO" button, similar to a green traffic light, and the instructions that they are cleared to proceed with searching for additional information.

2.B The second level of risk that is identified in the Fitness Triage® system is that of moderate potential risk. The user is advised that they have one or more conditions that may indicate a health problem. The user is strongly advised to seek professional health care advice and a physician's clearance before attempting any physical activity. This is graphically indicated to the user by use of a yellow "CAUTION" button, similar to a yellow traffic light.

2.C The third level of risk that is identified in the Fitness Triage® system is that of high potential risk. This is graphically indicated to the user by use of a red "STOP" button, similar to a red traffic light. The user is advised that they have one or more conditions that may indicate a health problem. They are strongly advised to seek professional health care advice and a physician's clearance before attempting any physical activity.

2.D Users receiving results at either the "Caution" or "Stop" level of potential risk will also be delivered information specific to the conditions they have indicated. For example, a user indicating diabetes will receive information regarding diabetes and exercise. The user is additionally advised that the information pages are not intended, and should not be used, as a substitute for proper medical advice and/or exercise prescription.

2.E Users receiving results from either of the three categories of potential risk may proceed with the process of seeking information from the Fitness gets Personal® database. This may be information on specific activities such as aqua aerobics or running, or on weight management or strength training, just to name a few of the possible topics.

FIG. 3

3.A The Fitness Gets Personal® database is composed of 3 primary content sources; 1) information covering over 90 subjects presented in a format of 1–2 page mini subject reports. In print format, these materials are referred to as Fitness Gets Personal® cards; 2) approximately 1000 fitness and health questions and appropriate answers; 3) a glossary of over 500 fitness and health terms and their definitions.

User selects 1 of 3 methods to search the Fitness Gets Personal® database: Keyword, topic in a category, or alphabetic.

3.B. Keyword. The user enters a keyword or short phrase, such as "diabetes", or "What is hypertension?"

3.C Matching questions are displayed, ranked by relevancy. As the user selects a question, the accompanying answer is displayed as well as links to related items, including the mini subject reports.

3.D Topic. The user first selects from 1 of 4 top-level categories: Exercise; Health & Safety; Lifestyle & Recreation; and Nutrition.

3.E After selecting a category, the user selects a topic from a list of topics within each category.

3.F A mini subject card on the matching content is displayed.

3.G Alphabetic. User selects a letter of the alphabet. All words or phrases contained in the glossary for that letter are displayed.

3.H User selects a word or short phrase.

3.I The definition is displayed along with links to related items, including the mini subject reports.

3.J User continues search or instigates a new search using 1 of the 3 methods.

3.K User may revise his Fitness Triage® profile on subsequent visits to the site. The system stores individual data and re-evaluates the fitness risk level each time that new information is introduced.

What is claimed is:

1. A data processing apparatus for delivering user-specific exercise and injury prevention information comprising:

a central controller including a CPU and a memory operatively connected to said CPU;

at least one terminal, adapted for communicating with said central controller for transmitting to said central controller, user-specific information selected from the group consisting of said user's prior and current health, medical and fitness conditions and habits;

said memory and said central controller containing a program, adapted to be executed by said CPU, for separately and collectively evaluating the risk associated with said user-specific information to determine whether said user may begin a fitness program;

wherein said central controller receives said information from said terminal and outputs a statement as to whether said user may begin a fitness program, and whether said user should obtain medical clearance before beginning such a program.

2. The apparatus of claim 1 wherein said memory and said central controller and said program enable a user who may begin a fitness program to access fitness information suitable for said user based on a keyword search, topic search and alphabetic search, or combination thereof, of information related to fitness and health questions and appropriate answers, and a glossary of fitness and health terms and their definitions.

3. A method of determining whether a user can begin a fitness program, and, if so, for determining an appropriate fitness program for said user using a central controller including a CPU and a memory operatively connected to said CPU and containing a program adapted to be executed by said CPU for determining whether said user may proceed with a fitness program, and, if so, for determining an appropriate fitness program for said user, the method comprising the steps of:

inputting user specific information about said user's prior and current health, medical and fitness conditions and habits; individually evaluating each of said health, medical and fitness conditions and habits for risk level; collectively evaluating said individual risk factors to determine whether said user may proceed with a fitness program, and, if said user can proceed, outputting a suitable fitness program for said user.

4. A data processing apparatus for determining whether a user may proceed with a fitness program, and, if so, for determining an appropriate fitness program for said user comprising: a CPU and a memory operatively connected to said CPU, said memory containing a program adapted to be executed by said CPU, said CPU and memory cooperatively adapted to receive user-specific inputs concerning said user's prior and current health, medical and fitness conditions and habits, and to determine, from said user-specific inputs, the risk associated with each of said inputs, and the collective risk to said user from the risks associated with each of said inputs to determine whether said user may proceed with a fitness program, or whether said user should seek medical advice before beginning such a fitness program.

5. A method of determining whether a user may begin a fitness program, or whether said user should first obtain medical advice before beginning such a program using a central controller including a CPU and a memory operatively connected to said CPU and containing a program adapted to be executed by said CPU for said determining steps, the method comprising the steps of:

inputting user-specific prior and current health, medical and fitness conditions and habits;

determining whether any of said conditions and habits are chronic or acute;

individually evaluating the risk associated with each of said inputs;

collectively evaluating the resulting individual risks;

determining whether said user may begin a fitness program, and, if so, with what limitations, or determining whether said user should obtain medical clearance before beginning a fitness program;

devising a fitness program appropriate for said user by having the CPU execute said program and outputting said appropriate fitness program.

6. The method of claim 5 further comprising opening to said user access to databases including information appropriate for a fitness program for said user.

7. A method for determining whether a user may begin a fitness program comprising the steps of:

receiving user-specific inputs concerning said user's prior and current health, medical and fitness conditions and habits relative to an appropriate fitness program for said user;

evaluating the risk associated with each of said inputs, and for evaluating these individual risks collectively; and outputting whether said user may proceed with a fitness program or should first obtain medical clearance before proceeding with a fitness program.

8. The method of claim 7 further comprising the step of outputting an appropriate fitness program for said user, if appropriate.

9. A data processing apparatus for determining whether a user can undertake a fitness program for said user comprising:

a terminal adapted to communicate with a central controller that determines and evaluates, collectively, the individual risks associated with each user-specific input about said user's prior and current health, medical and fitness conditions and habits and outputs the resulting information;

said terminal being adapted to transmit to said central controller said information and further adapted to receive from the central controller a decision as to whether said user may proceed with a fitness program or whether said user should first obtain medical advice before beginning a fitness program.

* * * * *